United States Patent
Matsubara

(10) Patent No.: US 10,157,461 B2
(45) Date of Patent: *Dec. 18, 2018

(54) CELL EVALUATION DEVICE, CELL EVALUATION METHOD, AND CELL EVALUATION PROGRAM

(71) Applicant: FUJIFILM Corporation, Tokyo (JP)

(72) Inventor: Kenta Matsubara, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 54 days.

This patent is subject to a terminal disclaimer.

(21) Appl. No.: 15/348,008

(22) Filed: Nov. 10, 2016

(65) Prior Publication Data

US 2017/0061618 A1    Mar. 2, 2017

Related U.S. Application Data

(63) Continuation of application No. PCT/JP2015/063884, filed on May 14, 2015.

(30) Foreign Application Priority Data

May 30, 2014    (JP) .................................. 2014-112135

(51) Int. Cl.
*G06K 9/00*    (2006.01)
*G06T 7/00*    (2017.01)
(Continued)

(52) U.S. Cl.
CPC .............. *G06T 7/0012* (2013.01); *C12Q 1/02* (2013.01); *C12M 41/36* (2013.01); *G06T 2207/10056* (2013.01); *G06T 2207/30024* (2013.01)

(58) Field of Classification Search
None
See application file for complete search history.

(56) References Cited

U.S. PATENT DOCUMENTS 5,828,776 A * 10/1998 Lee .................... G06K 9/00127
382/128
9,619,881 B2 * 4/2017 Maddah ................ G06T 7/0012
(Continued)

FOREIGN PATENT DOCUMENTS

JP    2011-24485 A    2/2011
JP    2011-229409 A    11/2011
(Continued)

OTHER PUBLICATIONS

Kong, H., Gurcan, M., & Belkacem-Boussaid, K. (2011). Partitioning histopathological images: an integrated framework for supervised color-texture segmentation and cell splitting. IEEE transactions on medical imaging, 30(9), 1661-1677.*
(Continued)

*Primary Examiner* — Vu Le
*Assistant Examiner* — Samah Beg
(74) *Attorney, Agent, or Firm* — Birch, Stewart, Kolasch & Birch, LLP

(57) ABSTRACT

The present invention provides a cell evaluation device, a cell evaluation method and a non-transitory computer readable recording medium storing a cell evaluation program capable of evaluating an evaluation target cell. The cell evaluation device includes an image acquisition unit that acquires a cell image obtained by imaging a cell group; a cell evaluation unit that specifies an evaluation target cell and peripheral cells around the evaluation target cell in the cell group, and evaluates the evaluation target cell based on evaluation results of the peripheral cells; and a boundary setting unit that sets a boundary in the cell image based on a state of the cell group, in which when specifying the
(Continued)

peripheral cells, the cell evaluation unit specifies only cells that are present in a divided region where the evaluation target cell is present among plural divided regions divided by the boundary, as the peripheral cells.

19 Claims, 9 Drawing Sheets

(51) Int. Cl.
*C12Q 1/02* (2006.01)
*C12M 1/34* (2006.01)

(56) References Cited

U.S. PATENT DOCUMENTS

| | | | |
|---|---|---|---|
| 2003/0179916 A1* | 9/2003 | Magnuson | C12Q 1/24 382/128 |
| 2005/0266395 A1* | 12/2005 | Gholap | G01N 33/5091 435/4 |
| 2006/0039593 A1* | 2/2006 | Sammak | G06K 9/00127 382/133 |
| 2011/0019897 A1* | 1/2011 | Takagi | G06T 7/0012 382/133 |
| 2011/0286654 A1* | 11/2011 | Krishnan | G06K 9/0014 382/133 |
| 2013/0071003 A1* | 3/2013 | Wirtz | G06K 9/00127 382/133 |
| 2013/0183707 A1* | 7/2013 | Mangoubi | G06F 19/24 435/29 |
| 2013/0236081 A1 | 9/2013 | Nakamura | |
| 2014/0064594 A1 | 3/2014 | Sugiyama et al. | |
| 2015/0187077 A1 | 7/2015 | Ozaki et al. | |
| 2015/0219543 A1* | 8/2015 | Yamauchi | G01N 15/10 356/335 |
| 2016/0161394 A1* | 6/2016 | Matsubara | C12Q 1/04 382/133 |
| 2016/0163049 A1* | 6/2016 | Matsubara | C12M 41/36 382/133 |
| 2016/0232682 A1* | 8/2016 | Nakagawa | C12M 41/36 |
| 2016/0335767 A1* | 11/2016 | Matsumoto | G06T 7/0012 |
| 2016/0364599 A1* | 12/2016 | Tsujimoto | G02B 21/14 |
| 2017/0081628 A1* | 3/2017 | Matsubara | C12M 1/34 |
| 2017/0146558 A1* | 5/2017 | Ishii | G01N 33/80 |
| 2017/0299370 A1* | 10/2017 | Rempel | G01N 21/359 |

FOREIGN PATENT DOCUMENTS

| | | | | |
|---|---|---|---|---|
| JP | 2011229409 A | * | 11/2011 | C12M 41/14 |
| JP | 2012-231709 A | | 11/2012 | |
| JP | 2014-39504 A | | 3/2014 | |
| WO | WO 2012/111236 A1 | | 8/2012 | |

OTHER PUBLICATIONS

International Search Report, issued in PCT/JP2015/063884, dated Jul. 28, 2015.
Written Opinion of the International Searching Authority, issued in PCT/JP2015/063884, dated Jul. 28, 2015.
International Preliminary Report on Patentability, issued in PCT/JP2015/063884, dated Dec. 6, 2016, with an English translation thereof.
Japanese Office Action issued in Japanese Application No. 2014-112135, dated Aug. 1, 2017, with an English translation.
Extended European Search Report dated Apr. 19, 2017 for corresponding EP Application No. 15799811.3.
Sarma, A.S.V,, "A Boundary Expansion Method for Analysis of Cell Neighborhoods and Identification of Cells in Plant Cross Sectional Images" 2013 International Conferene on Advanced Electronic Systems, IEEE, Sep. 21, 2013, pp. 243-247.

* cited by examiner

UNDIFFERENTIATED CELL    DIFFERENTIATED CELL

BOUNDARY

- PERIPHERAL RECTANGULAR REGION
- EVALUATION TARGET CELL
- PERIPHERAL CELL

CELL EVALUATION DEVICE, CELL
EVALUATION METHOD, AND CELL
EVALUATION PROGRAM

CROSS-REFERENCE TO RELATED
APPLICATIONS

This application is a Continuation of PCT International Application No. PCT/JP2015/063884 filed on May 14, 2015, which claims priority under 35 U.S.C § 119(a) to Japanese Patent Application No. 2014-112135 filed on May 30, 2014. Each of the above application(s) is hereby expressly incorporated by reference, in its entirety, into the present application.

BACKGROUND OF THE INVENTION

1. Field of the Invention

The present invention relates to a cell evaluation device, a cell evaluation method, and a non-transitory computer readable recording medium storing a cell evaluation program that evaluate individual cells in a cell image obtained by imaging a cell group.

2. Description of the Related Art

In the related art, a method for culturing multipotential stem cells, such as ES cells, iPS cells or STAP cells, or cells differentiated and induced therefrom or the like, imaging the cells using a microscope, and evaluating a state of the cells by grasping characteristics of an image obtained by the imaging has been proposed.

Here, the cultured cells are colonized according to the progress of the culture, and are proliferated into a large area. The size of a cell is an order of micrometers, and the size of a colony is an order of several millimeters to several centimeters.

When evaluating a cell group colonized in this way, it is important to evaluate individual cells in the colony. For example, in a transplanting process of regenerative medicine, in a case where undifferentiated cells are present together with differentiated cells, canceration may occur. Further, for example, in a case where multipotential stem cells are proliferated to be subcultured, it is necessary to cut out only undifferentiated cells.

As a method for evaluating individual cells, for example, JP2012-231709A discloses a method for comparing an inner optical path length of a cell nucleus with an outer optical path length thereof for an individual cell and evaluating whether the individual cell is a good stem cell based on the comparison result. Further, JP2012-231709A discloses a technique for setting a region where good stem cells in a cell colony are crowded as a good quality region.

Further, JP2014-39504A discloses a method for determining whether individual cells are nucleated erythrocytes (NRBCs) based on feature amounts calculated from images of the individual cells and learning parameters which are learned in advance.

SUMMARY OF THE INVENTION

However, when evaluating an individual cell based on a cell image obtained by imaging a cell group using a microscope as described above, if the evaluation is performed using only an image of each cell in a cell image, it may be impossible to appropriately perform the evaluation depending on visibility or the like of the cell image.

On the other hand, there is a tendency that a cell grows while having a relationship with peripheral cells to have the same characteristic as that of a peripheral cell group rather than acquiring a unique characteristic as a single cell. FIGS. 13A and 13B are enlarged views of a part of a cell image of a colonized cell group. A range surrounded by a solid line of FIG. 13A and a range surrounded by a broken line of FIG. 13B correspond to individual cells. As shown in FIGS. 13A and 13B, cells having similar shapes tend to be collected nearby.

Thus, when evaluating a predetermined evaluation target cell, it may be considered that evaluation results of peripheral cells of the evaluation target cell are referenced.

However, for example, as shown in FIG. 6, in a case where an evaluation target cell is present around a boundary between a region where cells in an undifferentiated state are distributed and a region where cells in a differentiated state are distributed, both the cells in the differentiated state and the cells in the undifferentiated state are present as peripheral cells of the evaluation target cell, and thus, there is a case where an undifferentiated state or differentiated state of the evaluation target cell is not appropriately evaluated.

In view of the above-mentioned problems, an object of the invention is to provide a cell evaluation device, a cell evaluation method, and a non-transitory computer readable recording medium storing a cell evaluation program capable of evaluating, when evaluating a predetermined evaluation target cell using evaluation results of peripheral cells thereof, the evaluation target cell with high accuracy.

According to the invention, there is provided a cell evaluation device including: an image acquisition unit that acquires a cell image obtained by imaging a cell group; a cell evaluation unit that specifies an evaluation target cell and peripheral cells around the evaluation target cell in the cell group, and evaluates the evaluation target cell based on evaluation results of the peripheral cells; and a boundary setting unit that sets a boundary in the cell image based on a state of the cell group, in which when specifying the peripheral cells, the cell evaluation unit is capable of specifying only cells are present in a divided region where the evaluation target cell is present among a plurality of divided regions divided by the boundary as the peripheral cells.

The cell evaluation device according to the invention may further include: an image pick-up condition acquisition unit that acquires an image pick-up condition different from an image pick-up condition of the cell image used in the evaluation in a case where it is determined that the evaluation is impossible to be performed when evaluating the evaluation target cell based on the evaluation results of the peripheral cells in the cell evaluation unit.

The image pick-up condition may include at least one of an image pick-up region, an exposure time, an optical magnification, an illumination light wavelength, or an observation light wavelength.

The cell evaluation unit may add identification information to a region where the peripheral cells specified when evaluating the evaluation target cell are present.

The image pick-up condition acquisition unit may acquire the image pick-up condition based on the cell image of the region to which the identification information is added.

The cell evaluation device may further include: a display controller that performs a control for displaying the image pick-up condition acquired by the image pick-up condition acquisition unit.

The cell evaluation device may further include: an image pick-up controller that outputs an imaging control signal according to the image pick-up condition acquired by the image pick-up condition acquisition unit.

The boundary setting unit may set the boundary based on at least one of a luminance, a spatial frequency, or a color of the cell image.

The boundary setting unit may set the boundary of which the number of inflection points or a curvature is limited.

According to the invention, there is provided a cell evaluation method including: acquiring a cell image obtained by imaging a cell group; and when specifying an evaluation target cell and peripheral cells around the evaluation target cell in the cell group and evaluating the evaluation target cell based on evaluation results of the peripheral cells, setting a boundary in the cell image based on a state of the cell group, and specifying only cells that are present in a divided region where the evaluation target cell is present among a plurality of divided regions divided by the boundary, as the peripheral cells.

According to the invention, there is provided a non-transitory computer readable recording medium storing a cell evaluation program that causes a computer to function as: an image acquisition unit that acquires a cell image obtained by imaging a cell group; a cell evaluation unit that specifies an evaluation target cell and peripheral cells around the evaluation target cell in the cell group, and evaluates the evaluation target cell based on evaluation results of the peripheral cells; and a boundary setting unit that sets a boundary in the cell image based on a state of the cell group, in which when specifying the peripheral cells, the cell evaluation unit specifies only cells that are present in a divided region where the evaluation target cell is present among a plurality of divided regions divided by the boundary, as the peripheral cells.

According to the cell evaluation device, the cell evaluation method, and the non-transitory computer readable recording medium storing a cell evaluation program of the invention, a cell image obtained by imaging a cell group is acquired; and when specifying an evaluation target cell and peripheral cells around the evaluation target cell in the cell group and evaluating the evaluation target cell based on evaluation results of the peripheral cells, a boundary in the cell image is set based on a state of the cell group, and only cells that are present in a divided region where the evaluation target cell is present among a plurality of divided regions divided by the boundary are specified as the peripheral cells. Thus, it is possible to specify cell having similar characteristics as peripheral cells, for example, without mixture of cells in an undifferentiated state and cells in a differentiated state as the peripheral cells as described above, and thus, it is possible to evaluate an evaluation target cell with high accuracy.

DESCRIPTION OF THE PREFERRED EMBODIMENTS

Figure 1:
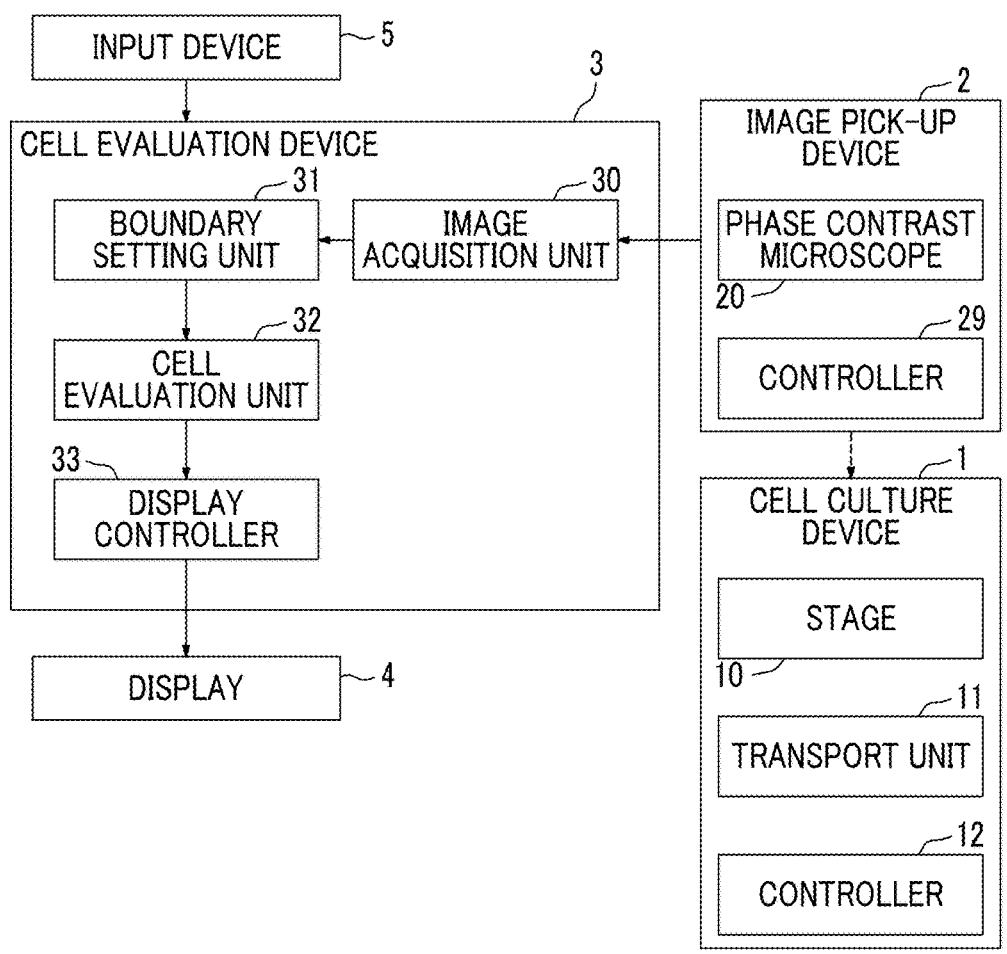
FIG. 1 is a block diagram showing a schematic configuration of a cell culture observation system using a cell evaluation device according to a first embodiment of the invention.

Hereinafter, a cell culture observation system using a cell evaluation device, a cell evaluation method and a non-transitory computer readable recording medium storing a cell evaluation program according to a first embodiment of the invention will be described with reference to the accompanying drawings. The invention has a feature in an evaluation method of individual cells in a cell image, but first of all, an entire configuration of the cell culture observation system of the first embodiment will be described. FIG. 1 is a block diagram showing a schematic configuration of the cell culture observation system.

As shown in FIG. 1, the cell culture observation system of this embodiment includes a cell culture device 1, an image pick-up device 2, a cell evaluation device 3, a display 4, and an input device 5.

The cell culture device 1 is a device for performing culture of cells. As culture target cells, for example, there are multipotential stem cells such as iPS cells, ES cells or STAP cells, cells such as nerves, skin, cardiac muscles or liver differentiated and induced from stem cells, cancer cells or the like. Plural culture vessels in which culture target cells are seeded in a culture medium are accommodated in the cell culture device 1. Further, the cell culture device 1 includes a stage 10, a transport unit 11, and a controller 12.

The stage 10 is a place where a culture vessel of an image pick-up target of the image pick-up device 2 is provided. And the transport unit 11 selects a culture vessel of an image pick-up target from plural culture vessels which are accommodated in predetermined positions in the cell culture device 1, and transports the selected culture vessel to the stage 10.

The controller 12 generally controls the cell culture device 1. The controller 12 moves the stage 10 in X-Y directions which are orthogonal to each other in an installation surface of a culture vessel. An image pick-up region of a phase contrast microscope 20 (which will be described later) is changed according to the movement.

Further, the controller 12 controls environmental conditions such as temperature, humidity, or $CO_2$ concentration and or the like in the cell culture device 1, in addition to an operation of the stage 10 or the transport unit 11. As a configuration for adjusting the temperature, the humidity, or the $CO_2$ concentration, a known configuration may be used.

The image pick-up device 2 captures an image of a cell group in a culture vessel provided on the stage 10. The image pick-up device 2 includes the phase contrast microscope 20 that images a cell group and outputs a cell image, and a controller 29 that controls the phase contrast microscope 20.

Figure 2:
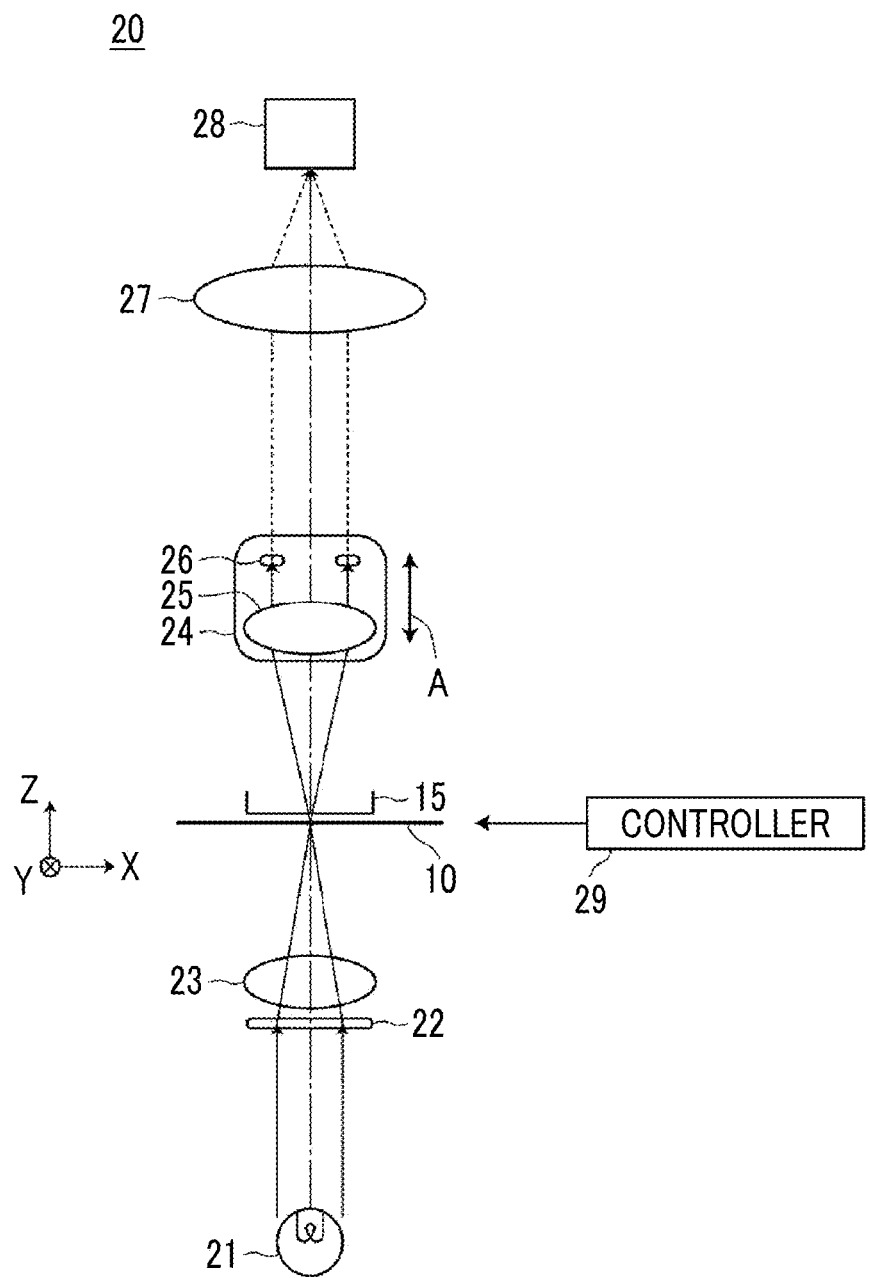
FIG. 2 is a diagram showing a schematic configuration of a phase contrast microscope.

The phase contrast microscope 20 captures a phase image of cells in a culture vessel provided on the stage 10. FIG. 2 is a diagram showing a schematic configuration of the phase contrast microscope 20. As shown in FIG. 2, the phase contrast microscope 20 includes an illumination light source 21 that emits illumination light, a slit plate 22 that has a ring-shaped slit, receives the illumination light emitted from the illumination light source 21 and incident thereto, and emits ring-shaped illumination light, and an objective lens 23 that receives the ring-shaped illumination light output from the slit plate 22 and incident thereto, and irradiates cells in the culture vessel 15 provided on the stage 10 with the incident ring-shaped illumination light.

Further, on a side opposite to the illumination light source 21 with respect to the stage 10, a phase contrast lens 24, an image forming lens 27, and an image pick-up element 28 are provided.

The phase contrast lens 24 includes an objective lens 25 and a phase plate 26. The phase plate 26 is an element in which a phase ring is formed with respect to a transparent plate which is transparent to wavelengths of the ring-shaped illumination light. The size of the slit of the above-mentioned slit plate 22 is in a conjugate relation with the phase ring.

The phase ring is an element in which a phase film that shifts a phase of incident light by a ¼ wavelength and a neutral density filter that dims the incident light are formed in a ring shape. Direct light incident to the phase contrast lens 24 is condensed by the objective lens 25 and passes through the phase ring, as a result, its phase shifts by a ¼ wavelength, and its brightness is weakened. On the other hand, diffracted light diffracted by the cells in the culture vessel 15 mostly passes through the transparent plate of the phase plate, and its phase and brightness do not change.

The phase contrast lens 24 moves in an arrow A direction shown in FIG. 2 by a drive mechanism (not shown). As the phase contrast lens 24 moves in this way, a focus position is changed, and thus, a focus control is performed. The drive mechanism moves the phase contrast lens 24 based on a focus control signal output from the controller 29.

Further, the phase contrast microscope 20 of this embodiment is configured so that plural phase contrast lenses 24 having different optical magnifications are exchangeable. The exchange of the phase contrast lenses 24 may be automatically performed based on a user's instruction input, or may be manually performed by a user.

The image forming lens 27 receives direct light and diffracted light passed through the phase contrast lens 24 and incident thereto, and forms an image of the direct light and the diffracted light in the image pick-up element 28. The image pick-up element 28 photoelectrically converts the image formed by the image forming lens 27 to image a phase image of cells. As the image pick-up element 28, a charge-coupled device (CCD) image sensor, a complementary metal-oxide semiconductor (CMOS) image sensor or the like may be used.

In this embodiment, the phase contrast microscope is used, but the invention is not limited thereto, and for example, a bright field microscope, a differential interference microscope or the like may be used.

The controller 29 generally controls the image pick-up device 2. Specifically, the controller 29 controls an optical magnification of the phase contrast microscope 20, an exposure time of the image pick-up element 28, an illumination light wavelength of the illumination light source, an observation light wavelength or the like. With respect to the illumination light wavelength of the illumination light source, for example, in a case where the illumination light source is configured by a light emitting diode (LED) or a laser diode (LD), the illumination light wavelength may be changed by changing a driving current thereof. Further, plural illumination light sources having different illumination light wavelengths may be provided and may be switched to change the illumination light wavelengths. In addition, the observation light wavelength may be changed using a filter (not shown), a spectroscope or the like.

The cell evaluation device 3 is a device in which a cell evaluation program according to an embodiment of the invention is installed in a computer.

The cell evaluation device 3 includes a central processing unit, a semiconductor memory, a hard disk and the like. The cell evaluation program according to the embodiment of the invention is installed in the hard disk. Further, as the cell evaluation program is executed by the central processing unit, an image acquisition unit 30, a boundary setting unit 31, a cell evaluation unit 32 and a display controller 33 as shown in FIG. 1 are operated.

The image acquisition unit 30 acquires and stores a cell image of a cell group imaged by the image pick-up device 2. In this embodiment, the image acquisition unit 30 acquires a cell image obtained by imaging a cell group with the optical magnification of the phase contrast microscope 20 being set to 4 times to 20 times.

The boundary setting unit 31 sets a boundary in a cell image based on a state of a cell group in the cell image. Specifically, for example, in a case where there are a region where stem cells in a differentiated state are distributed and a region where stem cells in an undifferentiated state are distributed in a cell group of the stem cells, the boundary setting unit 31 of this embodiment determines the differentiated region and the undifferentiated region, and sets a boundary between the differentiated region and the undifferentiated region.

Figure 3:
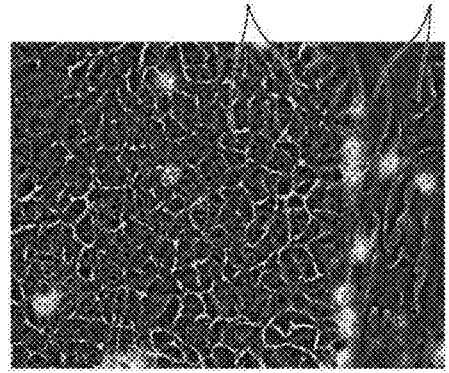
FIG. 3 is a diagram showing an example of a cell image of a cell group including stem cells in an undifferentiated state and stem cells in a differentiated state.

FIG. 3 is a diagram showing an example of a cell image of a cell group including stem cells in an undifferentiated state and stem cells in a differentiated state. As shown in FIG. 3, in the case of comparing the stem cells in the undifferentiated state with the stem cells in the differentiated state, the stem cells in the undifferentiated state have the degree of circularity higher than that of the stem cells in the differentiated state, and the stem cells in the differentiated state are more elongated than the stem cells in the undifferentiated state and have a maximum diameter larger than that of the stem cells in the undifferentiated state.

Accordingly, in consideration of a difference between the shapes of the stem cells in the differentiated state and the stem cells in the undifferentiated state, the boundary setting unit 31 calculates a spatial frequency of a cell image, and then, determines a region where the spatial frequency is equal to or greater than a predetermined threshold value as an undifferentiated region, and determines a region where the spatial frequency is smaller than the threshold value as a differentiated region.

Further, the boundary setting unit 31 may determine the differentiated region and the undifferentiated region using a luminance change or a color change, instead of the determination based on the spatial frequency of the cell image as described above. For example, as shown in FIG. 3, in the region where the stem cells in the undifferentiated state are distributed, the stem cells are densely distributed, and halo occurs in a boundary between the stem cells, so that the luminance becomes high. The halo represents a high luminance artifact generated when illumination light pass between cells.

On the other hand, in the region where the stem cells in the differentiated region are distributed, the differentiated stem cells are distributed over a culture medium, and a boundary between the stem cells is not so clear. Accordingly, the boundary setting unit 31 may calculate a luminance change of a cell image, and then, may determine a region where the luminance change is equal to or greater than a threshold value as an undifferentiated region, and may determine a region where the luminance change is smaller than the threshold value as a differentiated region. Further, a color change may be detected instead of the luminance change. That is, the boundary setting unit 31 may calculate a color change of a cell image, and then, may determine a region where the color change is equal to or greater than a predetermined threshold value as an undifferentiated region, and may determine a region where the color change is smaller than the threshold value as a differentiated region.

In addition, if growth of the cell group of the stem cells is progressed, the density of undifferentiated cells becomes high, and a region where the undifferentiated cells are layered and a region where the differentiated cells are distributed are formed. The luminance of the region where the undifferentiated cells are layered becomes higher than the luminance of the region where the differentiated cells are distributed. Accordingly, the boundary setting unit 31 may calculate the luminance of a cell image, and then, may determine a region where the luminance is equal to or greater than a predetermined threshold value as an undifferentiated region, and may determine a region where the luminance is smaller than the threshold value as a differentiated region.

Furthermore, the boundary setting unit 31 may determine the differentiated region and the undifferentiated region based on a combination of at least two characteristics of spatial frequency, luminance, or color. In this case, for example, the boundary setting unit 31 may calculate one evaluation value by weighting and adding up the plural characteristics, and then, may determine the differentiated region and the undifferentiated region according whether the evaluation value is equal to or greater than a threshold value or is smaller than the threshold value.

As described above, the boundary setting unit 31 of this embodiment calculates a feature amount for an entire cell image such as a spatial frequency, a luminance change, a color change or the like, and sets a boundary for generally dividing a cell group based on the feature amount.

Here, when setting the boundary between the differentiated region and the undifferentiated region based on at least one of spatial frequency, luminance or color of the cell image as described above, for example, there is a possibility that the halo portion where the luminance between the undifferentiated cells shown in FIG. 3 is high is set as the boundary, according to a threshold value setting method or the like. Further, since the purpose of setting boundary by the boundary setting unit 31 is for that an inappropriate cell is not included in peripheral cells when evaluating an evaluation target cell using a determination result of the peripheral cells as described above, a boundary for generally dividing the cell group is more favorable than a strict boundary, and it is preferable that a boundary having higher linearity is used.

Thus, for example, when setting a boundary, the boundary setting unit 31 may set an upper limit of the number of inflection points of the boundary, a curvature thereof or the like, and may set line segments having a smaller number of inflection points or a smaller curvature than the upper limit as the boundary. Specifically, for example, the boundary setting unit 31 may extract plural line segments which are boundary candidates, and may set a line segment that does not exceed the above-mentioned upper limit in the number of inflection points, the curvature or the like from the boundary candidates as a final boundary.

Figure 4:
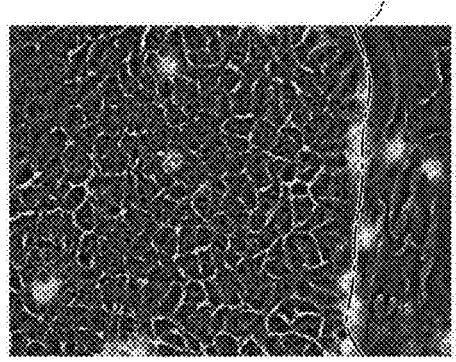
FIG. 4 is a diagram showing an example of a boundary set in the cell image shown in FIG. 3.

FIG. 4 is a diagram showing an example of a boundary set in the cell image shown in FIG. 3. In FIG. 4, a line segment indicated by a single-dot chain line represents a boundary set by the boundary setting unit 31.

Further, in the above description, the boundary setting unit 31 sets the boundary between the undifferentiated region and the differentiated region, but the boundary setting is not limited to the boundary between the undifferentiated region and the differentiated region. For example, in a case where a cell group includes cells that are differentiated and induced, the boundary setting unit 31 may set a boundary according to the degree of differentiation of the cells. For example, the boundary setting unit 31 may set a boundary between a region where the degree of differentiation is equal to or greater than a predetermined threshold value and a region where the degree of differentiation is smaller than the threshold value. In addition, in a case where the cell group includes cancer cells, the boundary setting unit 31 may set a boundary according to the degree of malignancy of the cancer cells. For example, the boundary setting unit 31 may set a boundary between a region where the degree of malignancy is equal to or greater than a threshold value and a region where the degree of malignancy is smaller than the threshold value.

Returning to FIG. 1, the cell evaluation unit 32 specifies an evaluation target cell and peripheral cells around the evaluation target cell in a cell group in a cell image, and evaluates the evaluation target cell based on evaluation results of the specified peripheral cells.

When evaluating states of individual cells based on a cell image as described above, if the states of the individual cells are evaluated based on only an image of the individual cells, there is a case where it is impossible to perform appropriate evaluation. Accordingly, when evaluating the evaluation target cell, the cell evaluation unit 32 acquires evaluation results of the peripheral cells either, and evaluates the evaluation target cell using the evaluation results of the peripheral cells and an evaluation result of the evaluation target cell. Hereinafter, a method for evaluating individual cells will be specifically described.

First, the cell evaluation unit 32 specifies individual cells included in a cell image. As a method for specifying individual cells, for example, a method for converting a cell image into a binarized image, detecting edges of the individual cells by performing a filter process, and performing pattern matching with respect to the edges to specify the individual cells may be used. Further, when performing the pattern matching, it is preferable to perform pattern recognition using machine learning. Here, the invention is not limited to this method, and may use various known methods.

Then, the cell evaluation unit 32 evaluates whether the individual cells specified as described above are in a differentiated state or in an undifferentiated state, respectively. Here, the cell evaluation unit 32 specifies peripheral cells around an evaluation target cell, and evaluates the evaluation target cell using evaluation results of the peripheral cells. Hereinafter, a method for specifying peripheral cells around an evaluation target cell will be described.

Figure 5:
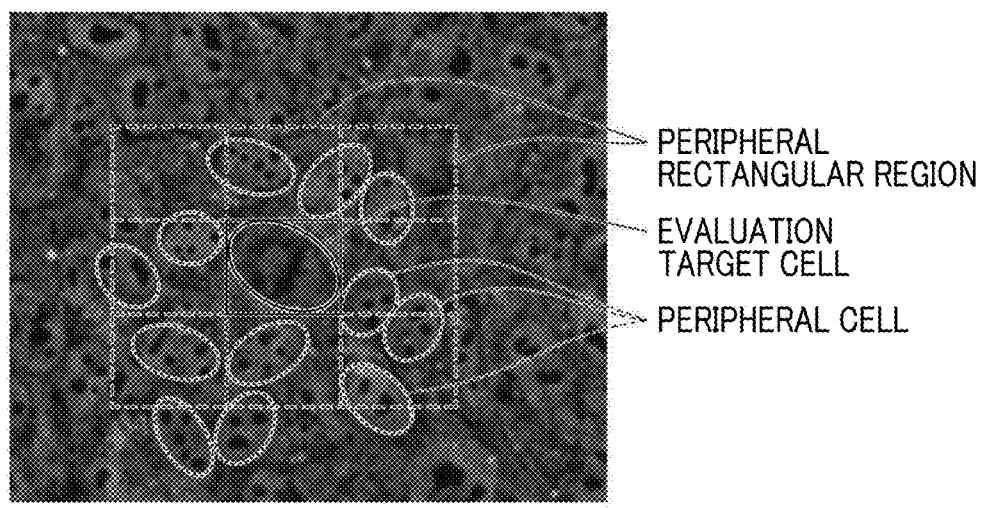
FIG. 5 is a diagram illustrating a method for specifying peripheral cells.

As the method for specifying the peripheral cells, for example, as shown in FIG. 5, a method for setting a rectangular region being in contact with the outline of a predetermined evaluation target cell (indicated by a solid-line oval), and setting rectangular regions having the same size as that of the set rectangular region around the rectangular region of the evaluation target cell, and specifying cells (indicated by dotted-line ovals) that are partly or totally included in the peripheral eight rectangular regions as peripheral cells may be used.

Figure 6:
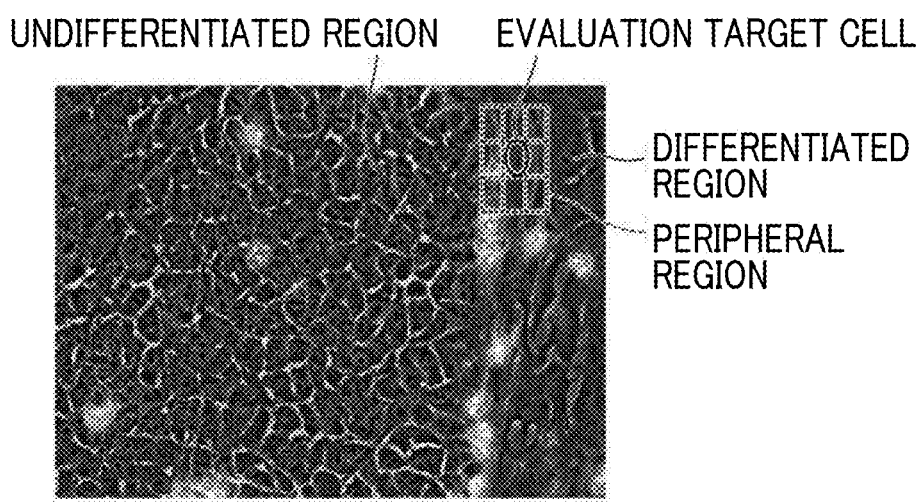
FIG. 6 is a diagram illustrating a method for specifying peripheral cells.

Here, as described above, when setting the peripheral regions around the evaluation target cell and specifying the cells included in the peripheral regions as the peripheral cells, for example, as shown in FIG. 6, in a case where the evaluation target cell is present in the vicinity of a boundary between an undifferentiated region and a differentiated region and the peripheral regions are set over the boundary, there is a case where both of cells in a differentiated state and cells in an undifferentiated state are present as the peripheral cells around the evaluation target cell and the undifferentiated state or differentiated state of the evaluation target cell is not appropriately evaluated.

Thus, the cell evaluation unit 32 of this embodiment acquires information about the boundary set in the boundary setting unit 31, and resets peripheral regions based on the boundary information.

Figure 7:
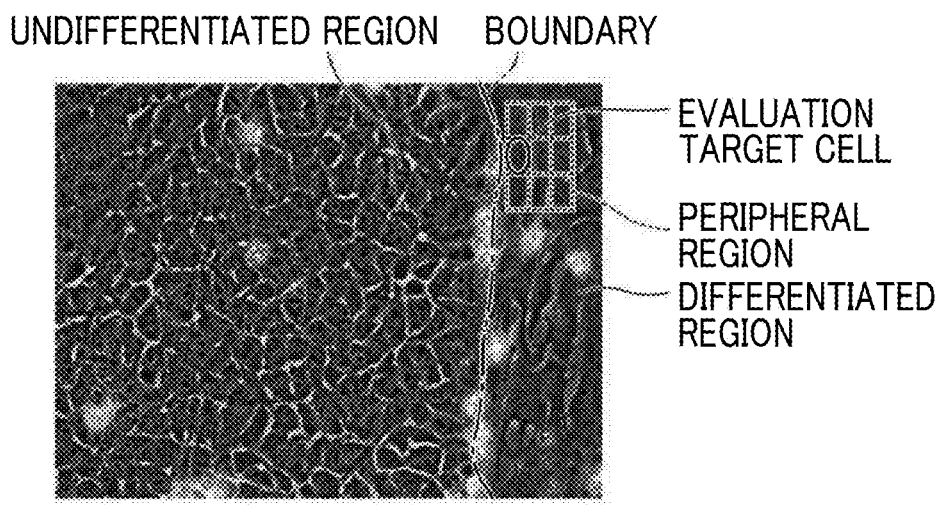
FIG. 7 is a diagram illustrating a method for specifying peripheral cells.

For example, as shown in FIG. 7, in a case where the evaluation target cell is present in the vicinity of the boundary and is a cell that is present within the differentiated region, the peripheral regions are reset so that only cells in the differentiated region are specified as the peripheral cells. Specifically, the above-mentioned eight rectangular regions are reset to be all disposed within the differentiated region. A method for resetting the peripheral regions is not limited to the example shown in FIG. 7, and any method may be employed as long as all the peripheral regions can be disposed in the differentiated region by the method.

By resetting the peripheral regions as described above, when evaluating the evaluation target cell, it is possible to use evaluation results of only cells within a region where the evaluation target cell is present, and thus, it is possible to evaluate an undifferentiated state or a differentiated state of the evaluation target cell with higher accuracy.

In the above description, the rectangular region being in contact with the outline of the evaluation target cell is set, and the rectangular regions having the same size as that of the set rectangular region are set around the evaluation target cell, that is, the sizes of the peripheral rectangular regions are set based on the size and shape of a cytoplasm of the evaluation target cell, but the invention is not limited thereto. For example, a method for detecting a cell nucleus or a nucleolus in an evaluation target cell, setting peripheral regions according to the size or shape of the cell nucleus or the nucleolus, and specifying cells included partly or totally in the peripheral regions as peripheral cells may be used.

Figure 8:
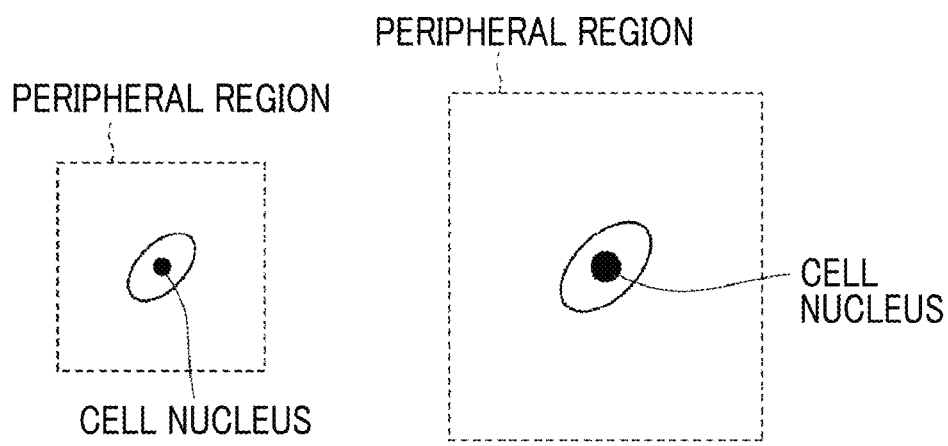
FIG. 8 is a diagram illustrating another method for setting a peripheral region of an evaluation target cell.
Figure 9:
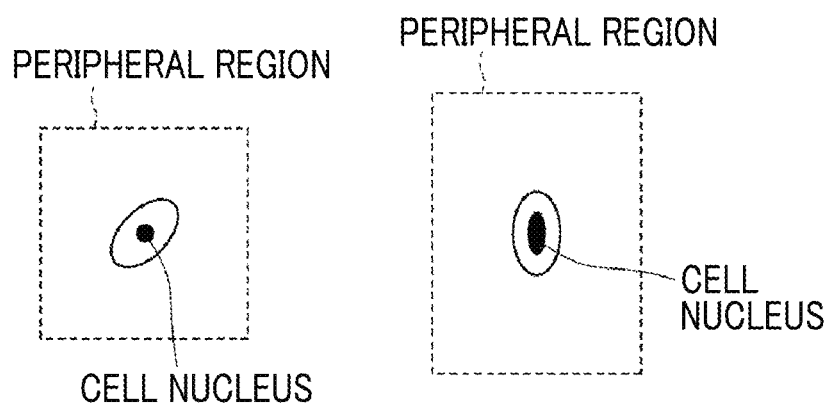
FIG. 9 is a diagram illustrating another method for setting a peripheral region of an evaluation target cell.

FIG. 8 is a diagram showing an example in which peripheral regions are set to become wider as a cell nucleus becomes larger. FIG. 9 is a diagram showing an example in which the shape of a peripheral region is set to be changed according to the shape of the cell nucleus. This is similarly applied to a case where the peripheral regions are set based on the size or shape of the nucleolus.

Further, in a case where plural cell images are captured in a time series manner instead of a configuration in which peripheral regions are set based on characteristics of cells in one cell image as described above, information relating to a proliferation rate of a cell, information relating to a migration rate thereof or the like may be acquired from the plural cell images, and peripheral regions may be set based on the information.

For example, in the case of a cell having a high proliferation rate, it may be considered that cells in a similar state are distributed in a wider range. Accordingly, as the proliferation rate becomes higher, larger peripheral regions may be set.

As a method for acquiring a cell proliferation rate, for example, a method for respectively counting the number of cells per unit area included in cell images captured at different time points and calculating a proliferation rate based on an increment of the number of cells and an image pick-up interval may be used. The unit area may be the entirety of a cell image or may be a partial region including an evaluation target cell.

Further, instead of the method for directly calculating the proliferation rate of the cell as described above, a method for respectively calculating areas of a cell group included in cell images captured at different time points and acquiring an area increasing rate as information relating to the proliferation rate may be used.

In addition, in the case of a cell having a high migration rate, it may be considered that cells in a similar state are distributed in a wider range. Accordingly, as the migration rate becomes higher, larger peripheral regions may be set.

As a method for acquiring a migration rate of a cell, for example, a method for calculating a movement distance of an evaluation target cell included in cell images captured at different time points and calculating a migration rate based on the movement distance and an image pick-up interval may be used.

With respect to matching of an evaluation target cell in cell images captured at different time points, for example, a method for matching cells having similar shapes which are present in a predetermined range may be used. Further, other known techniques may be used.

Further, instead of the method for calculating the migration rate of the evaluation target cell, a method for calculating a migration rate based on movement distances of all cells included in cell images may be used. For example, a method for calculating a statistic value such as an average value, a maximum value or a minimum value of movement distances of individual cells and calculating a migration rate based on the statistic value and an image pick-up interval may be used.

In addition, instead of the method for calculating the migration rate of the cell as described above, a method for acquiring the statistic value of the movement distances described above as information relating to the migration rate may be used.

Furthermore, when setting peripheral regions for specifying peripheral cells as described, each peripheral region may be enlarged until the number of peripheral cells included in the peripheral region reaches a predetermined number. By enlarging the peripheral region in this way, it is possible to specify a desired number of peripheral cells regardless of the density of cells, and thus, it is possible to stably enhance evaluation accuracy of an evaluation target cell.

When enlarging the peripheral region in this way, in a case where the peripheral region is a rectangular region, an aspect ratio between the enlarged length and width of the rectangular region may be 1, or may be a value different from 1. For example, in a case where the degree of circularity of a cytoplasm, a nucleus, or a nucleolus of an evaluation target is high to be close to a circle, the aspect ratio may be set to 1, and in a case where the shape thereof is an elliptical shape that extends in a longitudinal direction or a transverse direction, the aspect ratio may be set so that an enlarged width in the extending direction is relatively large.

Further, in a case where peripheral regions which are rectangular regions are set based on a proliferation rate, the aspect ratio may be set so that an enlarged width in a direction where the proliferation rate is high is relatively large. In addition, in a case where peripheral regions which are rectangular regions are set based on a migration rate, the aspect ratio may be set so that an enlarged width in a direction where the migration rate is high is relatively large.

Furthermore, as described above, when enlarging a peripheral region until the number of peripheral cells included in the peripheral region reaches a predetermined number, the number of cells that are investigated in the longitudinal direction and the number of cells that are investigated in the transverse direction may be equal to each other, or may be different from each other.

In a similar way to a case where the aspect ratio of the peripheral region is set as described above, for example, in a case where a cytoplasm, a nucleus, or a nucleolus of an evaluation target is close to a circle, the numbers of cells that are investigated in the longitudinal direction and the transverse direction may be set to be equal to each other, and in a case where the shape is an elliptical shape that extends in the longitudinal direction or the transverse direction, the number of cells that are investigated in the extending direction may be relatively large.

Further, in a case where peripheral regions which are rectangular regions are set based on a proliferation rate, the number of cells that are investigated in a direction where the proliferation rate is high may be relatively large. Furthermore, in a case where peripheral regions which are rectangular regions are set based on a migration rate, the number of cells that are investigated in a direction where the migration rate is high may be relatively large.

Hereinbefore, the method for specifying peripheral cells around an evaluation target cell has been described. In this embodiment, the peripheral cells are automatically specified as described above, but a user may designate peripheral cells using the input device 5, and the cell evaluation unit 32 receives designated information and thus may specify peripheral cells.

Then, the cell evaluation unit 32 sequentially specifies individual cells in a cell image as evaluation target cells, and sequentially specifies peripheral cells around the evaluation target cells, and evaluates each evaluation target cell using evaluation results of the peripheral cells.

The cell evaluation unit 32 of this embodiment evaluates whether an evaluation target cell is in a differentiated state or in an undifferentiated state as described above. Specifically, in this embodiment, the cell evaluation unit 32 calculates the degree of circularity of the evaluation target cell and the peripheral cells, evaluates that the evaluation target cell is in the undifferentiated state in a case where the degree of circularity is equal to or greater than a threshold value, and evaluates that the evaluation target cell is in the differentiated state in a case where the degree of circularity is smaller than the threshold value. Further, evaluation results of the evaluation target cell and the peripheral cells are stored together with positional information about the cells.

Here, the cell evaluation unit 32 evaluates whether the evaluation target cell is in the undifferentiated state or in the differentiated state based on the degree of circularity, but the evaluation based on the degree of circularity is not limited thereto. For example, the cell evaluation unit 32 may evaluate whether the evaluation target cell is in the undifferentiated state or in the differentiated state based on information about the size of a maximum diameter, a minimum diameter, an area or the like of individual cells, the density of a nucleolus included in each cell, or the like.

Further, the cell evaluation unit 32 may evaluate whether the evaluation target cell is in the differentiated state or in the undifferentiated state based on image information in a predetermined region including individual cells instead of characteristics of the shape of the individual cells as described above. For example, a method for calculating the density of cells in a predetermined region including an evaluation target cell, evaluating that the evaluation target cell is in the undifferentiated state in a case where the density is equal to or greater than a predetermined threshold value, and evaluating that the evaluation target cell is in the differentiated state in a case where the density is smaller than the threshold value may be used. In addition, a method may be used for calculating a statistic value such as an average value, a maximum value, a minimum value or the like of luminance in a predetermined region including an evaluation target cell, and evaluating that the evaluation target cell is in the undifferentiated state in a case where the statistic value of the luminance is smaller than a predetermined threshold value, and evaluating that the evaluation target cell is in the differentiated state in a case where the statistic value of the luminance is equal to or greater than the threshold value. In addition, the cell evaluation unit 32 may evaluate whether the evaluation target cell is in the undifferentiated state or in the differentiated state using other known methods.

Further, the cell evaluation unit 32 adds up the evaluation result of the evaluation target cell and the evaluation results of the peripheral cells, for example. In a case where the number of evaluation results in the undifferentiated state is larger, the cell evaluation unit 32 evaluates that the evaluation target cell is in the undifferentiated state, and in a case where the number of evaluation results in the differentiated state is larger, the cell evaluation unit 32 evaluates that the evaluation target cell is in the differentiated state.

Further, instead of the method for determining the evaluation result of the evaluation target cell according to the majority decision of the evaluation results, a method for calculating one evaluation value by weighting and adding up the evaluation result of the evaluation target cell and the evaluation results of the peripheral cells and determining an evaluation result of the evaluation target cell based on the evaluation value may be used.

Specifically, a method for setting the evaluation value to "2" in a case where the evaluation result is in the undifferentiated state and setting the evaluation value to "1" in a case where the evaluation result is in the differentiated state, calculating one evaluation value by adding up the evaluation value of the evaluation target cell and the evaluation values of the peripheral cells, and then, determining that the evaluation result of the evaluation target cell is in the undifferentiated state in a case where the evaluation value is equal to or greater than a predetermined threshold value and determining that the evaluation result of the evaluation target cell is in the differentiated state in a case where the evaluation value is smaller than the threshold value may be used.

Further, when adding up the evaluation value of the evaluation target cell and the evaluation values of the peripheral cells as described above, a weight larger than that of the evaluation values of the peripheral cells may be assigned to the evaluation value of the evaluation target cell for the adding up.

In addition, with respect to the evaluation values of the peripheral cells, weights may be changed according to distances from the evaluation target cell. For example, a larger weight of evaluation value of a peripheral cell that is closer to the evaluation target cell may be assigned.

Furthermore, when calculating the evaluation value of the evaluation target cell and the evaluation values of the peripheral cells as described above, for example, in a case where the undifferentiation and differentiation are evaluated based on the degree of circularity, and in a case where the degree of circularity shows an abnormal value out of a normal range, it is determined that the evaluation is impossible to be performed with respect to the concerned cell, and the evaluation value thereof may be set to "0". In this way, by setting the evaluation value of the cell that cannot be evaluated to "0", it is possible to evaluate the evaluation target cell using only evaluation results of cells of which evaluation results are fixed, and thus, it is possible to perform evaluation with higher accuracy.

As an example in which it is determined that a cell cannot be evaluated, for example, there is a case where the cell is a dead cell, or a case where a waste which is not a cell is misrecognized as a cell. Further, when evaluating the undifferentiation and differentiation based on the luminance in the vicinity of the evaluation target cell, in a case where a dead cell or a waste is included in the vicinity of the evaluation target cell, since a nucleolus of the dead cell is white and its luminance becomes abnormally high, and since the luminance of the waste may also become abnormally high, the evaluation value based on the luminance may become an abnormal value, and thus, it may be determined that the evaluation is impossible.

Thus, as described above, the cell evaluation unit 32 sequentially specifies individual cells included in a cell image as evaluation target cells, and sequentially specifies peripheral cells to perform evaluation, but in this case, with respect to a cell which is evaluated once, the cell evaluation unit 32 may not perform evaluation and may use the stored evaluation result. Thus, it is possible to simplify the evaluation process, and to perform the evaluation process at high speed.

In the above description, a configuration in which the cell evaluation unit 32 evaluates whether the evaluation target cell is in the undifferentiated state or in the differentiated state is shown, but the invention is not limited thereto. For example, a configuration in which in a case where a cell group includes differentiated and induced cells, the degrees of differentiation of the cells are evaluated may be used. In this case, for example, a method for expressing stages of the degrees of differentiation as numerical values based on shapes or the like of individual cells, calculating a statistic value such as an average value, a maximum value, or a minimum value of the degree of an evaluation target cell and the degrees of differentiation of peripheral cells, and determining the statistic value as the degree of differentiation of the evaluation target cell may be used. Further, in this case, weighting and adding up may be performed according to distances between the evaluation target cell and the peripheral cells. In addition, in a case where the cell group includes cancer cells, the degree of malignancy of the cells may be evaluated.

The display controller 33 acquires a cell image read from the image acquisition unit 30, acquires evaluation results of individual cells evaluated in the cell evaluation unit 32, and displays the cell image and the evaluation results on the display 4. As a method for displaying the evaluation results of the individual cells, for example, a method for displaying an evaluation result of a cell designated by a user using the input device 5 as a text may be used, or a method for mapping evaluation results of individual cells using different colors, for example, to generate a cell evaluation image and superimposing the cell evaluation image on the cell image for display may be used. As the cell evaluation image, a semi-transparent image capable of transmitting the cell image so that the cell image can be observed may be used, or an image in which outlines of individual cells are expressed using different colors or the like may be used.

The input device 5 includes a mouse, a keyboard or the like, and receives setting inputs from a user. For example, the input device 5 is able to receive setting inputs such as image pick-up conditions of an optical magnification or the like of the phase contrast microscope 20, designation information of individual cells in a cell image, or the like.

Figure 10:
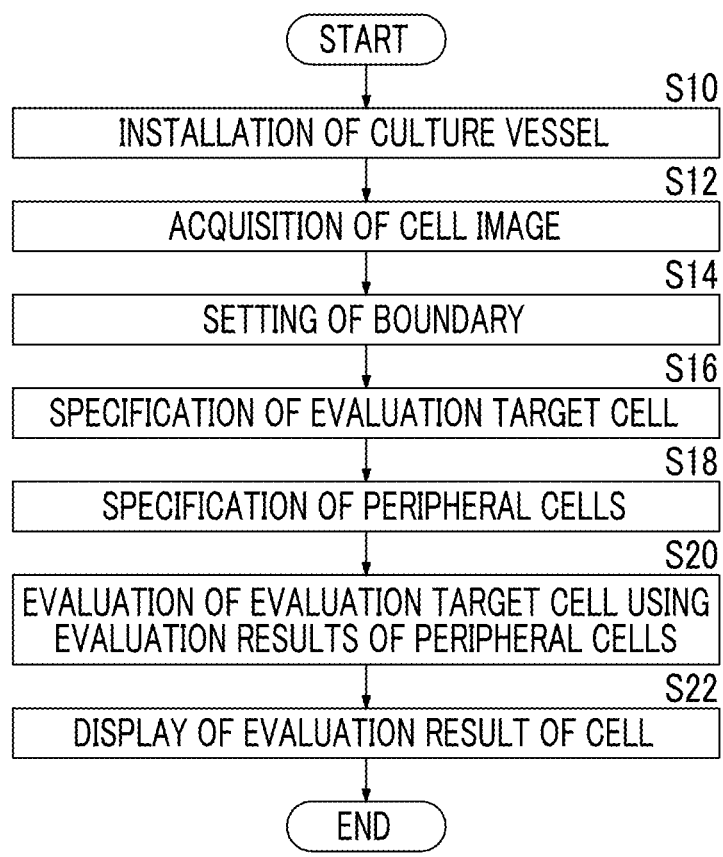
FIG. 10 is a flowchart illustrating an operation of the cell culture observation system using the cell evaluation device according to the first embodiment of the invention.

Next, an operation of the above-described cell culture observation system will be described with reference to the flowchart shown in FIG. 10.

First, in the cell culture device 1, a culture vessel which is an image pick-up target is selected from plural accommodated culture vessels by the transport unit 11, and the selected culture vessel is installed in the stage 10 (S10).

Further, an image of a cell colony in the culture vessel is captured by the phase contrast microscope 20 of the image pick-up device 2, and the captured cell image is acquired by the image acquisition unit 30 of the cell evaluation device 3 (S12).

Then, the cell image acquired by the image acquisition unit 30 is read out by the boundary setting unit 31, and the boundary setting unit 31 sets a boundary in the cell image based on the state of a cell group in the cell image (S14). In this embodiment, a boundary between a differentiated region and an undifferentiated region is set as described above.

Information about the boundary set in the boundary setting unit 31 is output to the cell evaluation unit 32, and the cell evaluation unit 32 specifies individual cells in the cell image (S16), and specifies peripheral cells based on the input boundary information (S18).

Further, the cell evaluation unit 32 sequentially specifies the individual cells in the cell image as evaluation target cells, sequentially specifies the peripheral cells, and evaluates the evaluation target cells using evaluation results of the peripheral cells (S20).

Evaluation results of individual cell regions evaluated in the cell evaluation unit 32 are output to the display controller 33, and the display controller 33 displays the cell image and the evaluation results of the individual cells on the display 4 (S22).

Next, a cell culture observation system of a cell evaluation device according to a second embodiment of the invention will be described.

In the cell culture observation system according to the first embodiment, when evaluating an evaluation target cell using evaluation results of peripheral cells, an evaluation result of a cell that cannot be evaluated among evaluation results of the evaluation target cell and the peripheral cells is not used. However, in the cell culture observation system according to the second embodiment, in a case where there is a cell that cannot be evaluated, the cell that cannot be evaluated is re-evaluated using cell images captured under image pick-up conditions different from those of a cell image including the cell that cannot be evaluated.

Figure 11:
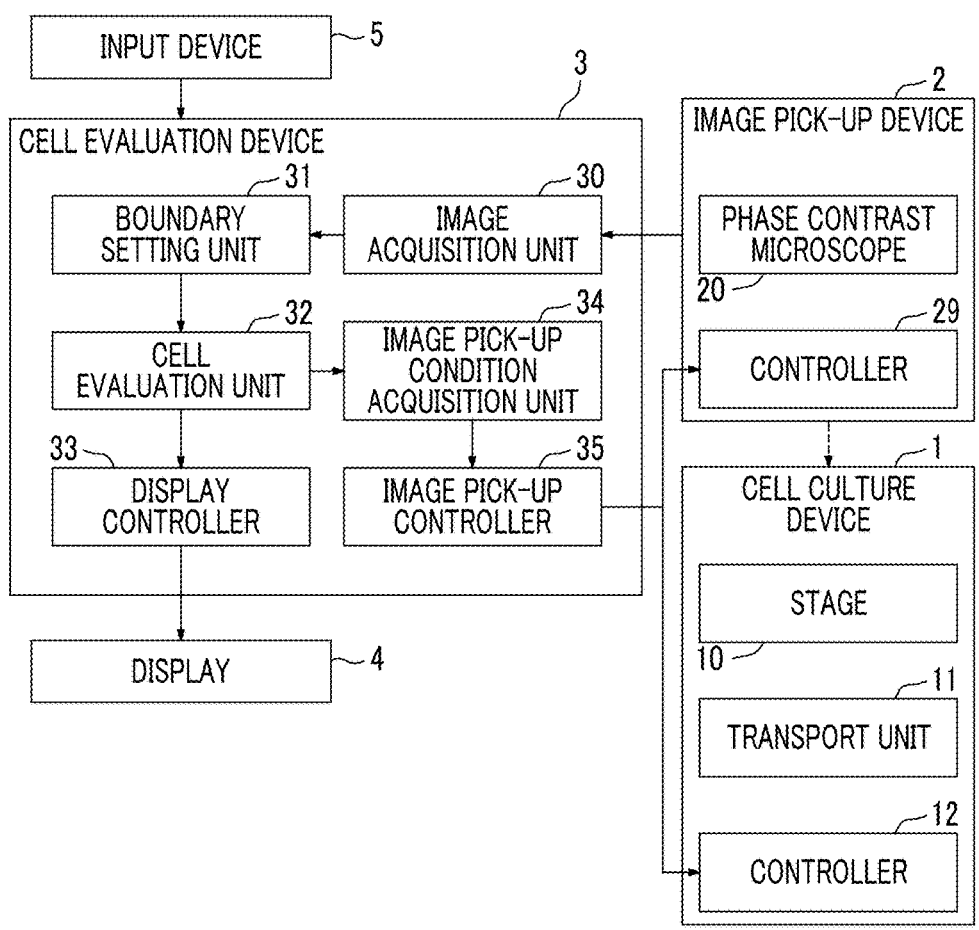
FIG. 11 is a block diagram showing a schematic configuration of a cell culture observation system using a cell evaluation device according to a second embodiment of the invention.

Specifically, as shown in FIG. 11, the cell culture observation system according to the second embodiment further includes an image pick-up condition acquisition unit 34 and an image pick-up controller 35.

Further, when evaluating an evaluation target cell using evaluation results of peripheral cells, in a case where a cell that cannot be evaluated is included in the evaluation target cell and peripheral cells, the cell evaluation unit 32 in the cell culture observation system according to the second embodiment assigns identification information to an evaluation target region including the evaluation target cell and the peripheral cells for storage. The identification information is identification information indicating that a cell that cannot be evaluated is included in an evaluation target region.

In a case where the above-mentioned evaluation target region to which the identification information is assigned by the cell evaluation unit 32 is present, the image pick-up condition acquisition unit 34 acquires image pick-up conditions when re-imaging a cell image used for re-evaluation of the evaluation target region.

Specifically, the image pick-up condition acquisition unit 34 acquires an optical magnification higher than an optical magnification when capturing a cell image including a cell that cannot be evaluated. Specifically, for example, a cell image for which an optical magnification is 4 may be used in an initial evaluation, and a cell image for which an optical magnification is 20 may be used in re-evaluation. Image pick-up conditions when capturing a cell image including the cell that cannot be evaluated are stored together with the cell image. Further, image pick-up conditions in re-imaging are also set in advance.

Further, the image pick-up condition acquisition unit 34 may acquire other image pick-up conditions other than the above-described optical magnification. As other image pick-up conditions, for example, an image pick-up region, an image pick-up timing, an exposure time of an image pick-up element, an illumination light wavelength, an observation light wavelength, or the like may be used.

With respect to the image pick-up region, a method for changing the image pick-up region to a narrow range according to change in an optical magnification when performing re-imaging may be used.

Further, with respect to the image pick-up timing, for example, a method for setting, in a case where an image pick-up timing when capturing a cell image including a cell that cannot be evaluated is a culture initial stage, an image pick-up timing of re-imaging to a culture termination time may be used. Further, contrarily, a method for acquiring an image pick-up timing prior to the image pick-up timing when the cell image including the cell that cannot be evaluated is captured may be used. That is, re-evaluation may be performed using a previously captured cell image. The image pick-up timing may be measured using a timer or the like, for example. Further, it is preferable that the image pick-up timing is set to a timing that matches a cell division cycle.

In addition, with respect to the exposure time of the image pick-up element, a method for setting the exposure time to be long to raise S/N of a cell image in re-imaging and setting the exposure time to be short to lower the luminance of the cell image in a case where a waste having an abnormally high luminance is present may be used.

Further, with respect to the illumination light wavelength, for example, a method for setting the illumination light wavelength to be short to enhance the resolution of a cell image, in re-imaging, may be used. Contrarily, a method for setting the illumination light wavelength to be long to reduce scattered light and to re-capture a cell image with less blur may be used.

Further, with respect to the observation light wavelength, for example, a method for changing wavelengths using a filter or a spectroscope, in re-imaging, may be used.

In addition, in the above description, a configuration in which the image pick-up conditions of re-imaging are set in advance with respect to the image pick-up condition acquisition unit 34, but the invention is not limited thereto, and a configuration in which the image pick-up condition acquisition unit 34 automatically determines and acquires image pick-up conditions using a cell image of an evaluation target region including a cell that cannot be evaluated may be used.

Specifically, for example, a method for determining and acquiring, in a case where the sizes of individual cells included in the cell image of the evaluation target region are equal to or smaller than a predetermined threshold value, a high optical magnification at which the sizes of individual cells become larger than the predetermined threshold value may be used. Further, with respect to the image pick-up timing, for example, a method for predicting a culture period from densities or the like of individual cells in a cell image of an evaluation target region, and determining and acquiring an image pick-up timing of re-imaging based on a predetermined culture cycle or the like using the culture period as a reference may be used.

Further, with respect to the exposure time of the image pick-up element, a method for acquiring S/N of a cell image of an evaluation target region and setting, in a case where the S/N is equal to or smaller than a predetermined threshold value, the exposure time to be long to raise the S/N of the cell image may be used. In addition, a method for acquiring a statistic value such as an average value, a maximum value, a minimum value, or the like of luminance of a cell image of an evaluation target region, and setting, in a case where the statistic value is equal to or greater than a predetermined threshold value, the exposure time to be short to lower the luminance of the cell image may be used.

Furthermore, with respect to the illumination light wavelength, a method for acquiring the resolution of a cell image of an evaluation target region and setting, in a case where the resolution is equal or smaller than a predetermined threshold value, the illumination light wavelength to be short to enhance the resolution of the cell image may be used. A method for acquiring blur of the cell image of the evaluation target region and setting, in a case where the degree of blur is equal to or greater than a predetermined degree, the illumination light wavelength to be long to reduce the blur of the cell image may be used. Further, with respect to the observation light wavelength, similarly, a method for acquiring the resolution or blur from a cell image to change the resolution or blur may be used.

The image pick-up controller 35 acquires image pick-up conditions of re-imaging acquired in the image pick-up condition acquisition unit 34, and outputs an imaging control signal to the controller 29 of the image pick-up device 2 or the controller 12 of the cell culture device 1 based on the image pick-up conditions. The controller 29 of the image pick-up device 2 controls an optical magnification, an exposure time of the image pick-up element, an image pick-up timing, an illumination light wavelength, and an observation light wavelength based on the imaging control signal output from the image pick-up controller 35. Further, the controller 12 of the cell culture device 1 controls an image pick-up region by moving the stage 10 based on the imaging control signal output from the image pick-up controller 35.

Figure 12:
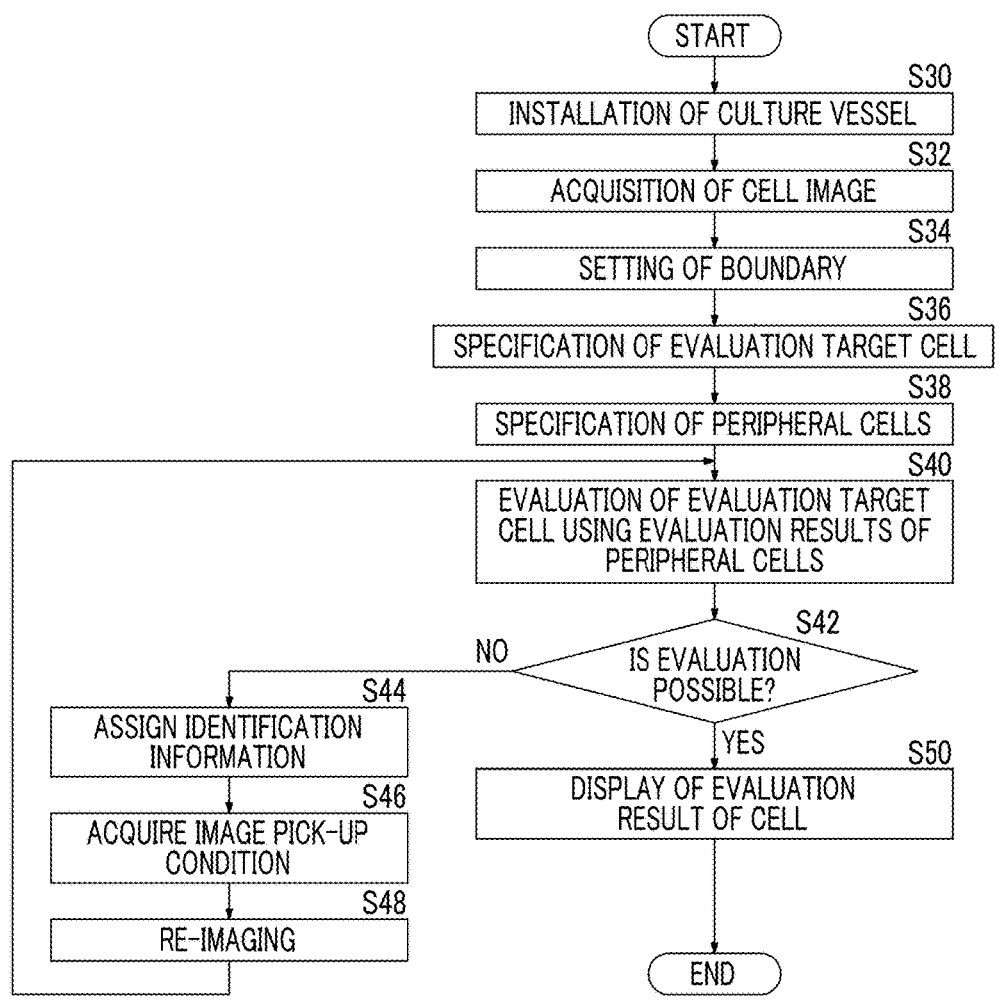
FIG. 12 is a flowchart illustrating an operation of the cell culture observation system using the cell evaluation device according to the second embodiment of the invention.
Figure 13A:
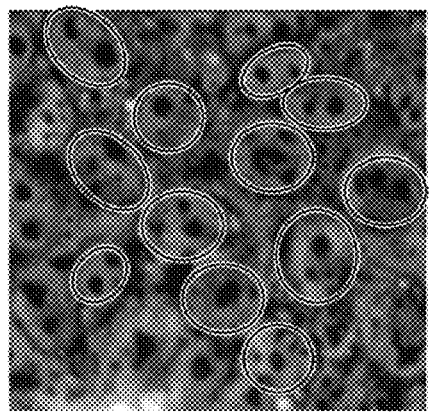
FIGS. 13A and 13B are diagrams showing an example of cell images in a state where similar cells are distributed.
Figure 13B:
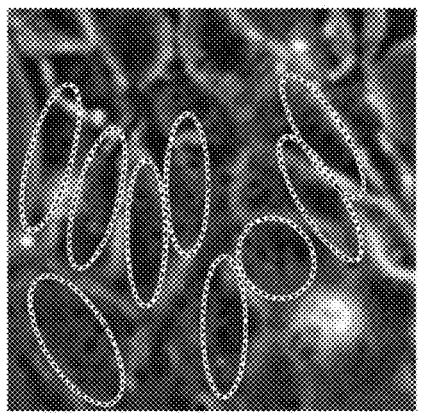

Next, an operation of the cell culture observation system according to the second embodiment will be described with reference to the flowchart shown in FIG. 12.

In the cell culture observation system according to the second embodiment, similarly, operations (S30 to S38) for specifying individual cells in a cell image and specifying peripheral cells based on input boundary information are the same as in the cell culture observation system according to the first embodiment.

Further, the cell evaluation unit 32 sequentially specifies the individual cells in the cell image as evaluation target cells, sequentially specifies peripheral cells of the evaluation target cells, and evaluates each evaluation target cell using evaluation results of the peripheral cells (S40). When performing the evaluation, in a case where there is a cell that cannot be evaluated in the evaluation target cells and the peripheral cells (NO in S42), identification information is assigned to the corresponding evaluation target region for storage (S44).

Further, in a case where there is an evaluation target region where the above-described identification information is assigned after all the individual cells are evaluated, positional information or the like of the evaluation target region is output to the image pick-up condition acquisition unit 34 from the cell evaluation unit 32, and the image pick-up condition acquisition unit 34 acquires image pick-up conditions of re-imaging for the evaluation target region (S46).

The image pick-up conditions acquired by the image pick-up condition acquisition unit 34 are output to the image pick-up controller 35, and the image pick-up controller 35 outputs an imaging control signal to the controller 29 of the image pick-up device 2 or the controller 12 of the cell culture device 1 based on the input image pick-up conditions. Further, re-imaging is performed under the control of the controller 29 of the image pick-up device 2 or the controller 12 of the cell culture device 1, and a cell image having image pick-up conditions different from those of the cell image used in the previous evaluation is acquired (S48).

The cell image acquired through the re-imaging is input to the cell evaluation unit 32 again, and re-evaluation is performed with respect to an evaluation target region including a cell that cannot be evaluated (S40). Further, in a case where there is no cell that cannot be evaluated (YES in S42), evaluation results of individual cell regions are output to the display controller 33, and the display controller 33 displays the cell image and the evaluation results of the individual cells on the display 4 (S50). Even in a case where a cell that cannot be evaluated through the above-described re-imaging is not removed, a message or the like indicating such a fact may be displayed on the display 4 to then terminate the procedure.

According to the cell culture observation system according to this embodiments, when evaluating individual cells using a cell image captured under predetermined image pick-up conditions, even in a case where a cell that cannot be evaluated are present, since re-imaging is performed under different image pick-up conditions and re-evaluation is performed using a re-captured cell image, it is possible to evaluate individual cells with high accuracy.

In the cell culture observation system according to the second embodiment, a configuration in which the image pick-up condition acquisition unit 34 automatically acquires image pick-up conditions is shown, but the invention is not limited thereto. For example, a configuration in which a user inputs image pick-up conditions of re-imaging using the input device 5 and the image pick-up condition acquisition unit 34 acquires the input image pick-up conditions may be used.

Furthermore, in the cell culture observation system according to the second embodiment, a configuration in which the image pick-up controller 35 automatically performs re-imaging based on image pick-up conditions acquired the image pick-up condition acquisition unit 34 is shown, but the invention is not limited thereto. For example, a configuration in which the display controller 33 displays image pick-up conditions acquired by the image pick-up condition acquisition unit 34 on the display 4 to request a user to perform re-imaging, and accordingly, the user manually performs the re-imaging may be used.

EXPLANATION OF REFERENCES

1: cell culture device
2: image pick-up device
3: cell evaluation device
4: display
5: input device
10: stage
11: transport unit
12: controller
15: culture vessel
20: phase contrast microscope
21: illumination light source
22: slit plate
23: objective lens
24: phase contrast lens
25: objective lens
26: phase plate
27: image forming lens
28: image pick-up element
29: controller
30: image acquisition unit
31: boundary setting unit
32: cell evaluation unit
33: display controller
34: image pick-up condition acquisition unit
35: image pick-up controller

What is claimed is:

1. A cell evaluation device for evaluating cultured cells, comprising:
   a central processing unit that:
   acquires a cell image obtained by imaging a cell group,
   specifies an evaluation target cell and peripheral cells around the evaluation target cell in the cell group,
   evaluates the evaluation target cell based on evaluation results of the peripheral cells, and
   sets a boundary in the cell image based on a state of the cell group;
   wherein when the central processing unit specifies the peripheral cells, the central processing unit specifies only cells that are present in a divided region where the evaluation target cell is present among a plurality of divided regions divided by the boundary, as the peripheral cells; and
   when the central processing unit evaluates the evaluation target cell based on the evaluation results of the peripheral cells, in a case where it is determined that the evaluation is impossible to be performed, the central processing unit acquires an image pick-up condition different from an image pick-up condition of the cell image used in the evaluation; and
   acquires a new cell image using the different acquired image pick-up condition.

2. The cell evaluation device according to claim 1,
wherein the image pick-up condition includes at least one of an image pick-up region, an exposure time, an optical magnification, an illumination light wavelength, or an observation light wavelength.

3. The cell evaluation device according to claim 2,
wherein the central processing unit adds identification information to a region where the peripheral cells specified when evaluating the evaluation target cell are present.

4. The cell evaluation device according to claim 3,
wherein the central processing unit acquires the image pick-up condition based on a cell image of a region to which the identification information is added.

5. The cell evaluation device according to claim 4, wherein the central processing unit further performs a control for displaying the image pick-up condition acquired by the image pick-up condition acquisition unit.

6. The cell evaluation device according to claim 3,
wherein the central processing unit further performs a control for displaying the image pick-up condition acquired by the central processing unit.

7. The cell evaluation device according to claim 2,
wherein the central processing unit further performs a control for displaying the image pick-up condition acquired by the central processing unit.

8. The cell evaluation device according to claim 2,
wherein the central processing unit further outputs an imaging control signal according to the image pick-up condition acquired by the central processing unit.

9. The cell evaluation device according to claim 1,
wherein the central processing unit adds identification information to a region where the peripheral cells specified when evaluating the evaluation target cell are present.

10. The cell evaluation device according to claim 9,
wherein the central processing unit acquires the image pick-up condition based on a cell image of a region to which the identification information is added.

11. The cell evaluation device according to claim 10, wherein the central processing unit further performs a control for displaying the image pick-up condition acquired by the central processing unit.

12. The cell evaluation device according to claim 9, wherein the central processing unit performs a control for displaying the image pick-up condition acquired by the central processing unit.

13. The cell evaluation device according to claim 9,
wherein the central processing unit further outputs an imaging control signal according to the image pick-up condition acquired by the central processing unit.

14. The cell evaluation device according to claim 1,
wherein the central processing unit further performs a control for displaying the image pick-up condition acquired by the central processing unit.

15. The cell evaluation device according to claim 1,
wherein the central processing unit further outputs an imaging control signal according to the image pick-up condition acquired by the central processing unit.

16. The cell evaluation device according to claim 1,
wherein the central processing unit sets the boundary based on at least one of a luminance, a spatial frequency, or a color of the cell image.

17. The cell evaluation device according to claim 1,
wherein the central processing unit sets the boundary of which the number of inflection points or a curvature is limited.

18. A cell evaluation method for evaluating cultured cells using the cell evaluation device according to claim 1 comprising:
acquiring a cell image obtained by imaging a cell group; and
specifying an evaluation target cell and peripheral cells around the evaluation target cell in the cell group and evaluating the evaluation target cell based on evaluation results of the peripheral cells, and
setting a boundary in the cell image based on a state of the cell group,
wherein when specifying the peripheral cells, specifying only cells that are present in a divided region where the evaluation target cell is present among a plurality of divided regions divided by the boundary, as the peripheral cells,
wherein when evaluating the evaluation target cell based on the evaluation results of the peripheral cells, in a case where it is determined that the evaluation is impossible to be performed, then acquiring an image pick-up condition different from an image pick-up condition of the cell image used in the evaluation, and
acquiring a new cell image using the different acquired image pick-up condition.

19. A non-transitory computer readable recording medium storing a cell evaluation program for evaluating cultured cells that causes a computer to function as:
an image acquisition unit that acquires a cell image obtained by imaging a cell group;
a cell evaluation unit that specifies an evaluation target cell and peripheral cells around the evaluation target cell in the cell group and evaluates the evaluation target cell based on evaluation results of the peripheral cells;
a boundary setting unit that sets a boundary in the cell image based on a state of the cell group;
wherein when specifying the peripheral cells, the cell evaluation unit specifies only cells that are present in a divided region where the evaluation target cell is present among a plurality of divided regions divided by the boundary, as the peripheral cells;
an image pick-up condition acquisition unit that acquires an image pick-up condition different from an image pick-up condition of the cell image used in the evaluation in a case where it is determined that the evaluation is impossible to be performed when evaluating the evaluation target cell based on the evaluation results of the peripheral cells in the cell evaluation unit, and
wherein the image acquisition unit acquires a new cell image using the different acquired image pick-up condition.

* * * * *